US007588533B2

(12) United States Patent
Drysdale

(10) Patent No.: US 7,588,533 B2
(45) Date of Patent: Sep. 15, 2009

(54) SEXUAL THERAPY DEVICE

(76) Inventor: Joanne Drysdale, 145 E. 900 N., Price, UT (US) 84501

( * ) Notice: Subject to any disclaimer, the term of this patent is extended or adjusted under 35 U.S.C. 154(b) by 587 days.

(21) Appl. No.: 11/285,981

(22) Filed: Nov. 23, 2005

(65) Prior Publication Data

US 2006/0116612 A1 Jun. 1, 2006

Related U.S. Application Data

(60) Provisional application No. 60/631,251, filed on Nov. 26, 2004.

(51) Int. Cl.
*A61F 5/00* (2006.01)

(52) U.S. Cl. .......................................................... 600/38

(58) Field of Classification Search ............. 600/38–41; 601/6–14

See application file for complete search history.

(56) References Cited

U.S. PATENT DOCUMENTS

| | | | | |
|---|---|---|---|---|
| 2,314,590 | A | 3/1943 | McCarty | |
| 2,978,733 | A | 4/1961 | Wahlborg | |
| 3,382,867 | A * | 5/1968 | Reaves | 601/7 |
| 4,961,245 | A | 10/1990 | Barnes, Jr. et al. | |
| 5,094,230 | A | 3/1992 | Clark, Jr. | |
| 5,336,158 | A | 8/1994 | Huggins et al. | |
| 5,669,869 | A | 9/1997 | Strom | |
| 5,693,002 | A | 12/1997 | Tucker et al. | |
| 6,099,463 | A | 8/2000 | Hockhalter | |
| D443,057 | S | 5/2001 | Hovland et al. | |
| 6,248,059 | B1 | 6/2001 | Gamper et al. | |
| 6,464,653 | B1 | 10/2002 | Hovland et al. | |
| 6,733,438 | B1 | 5/2004 | Dann et al. | |
| 6,875,198 | B2 * | 4/2005 | Foley | 604/119 |

FOREIGN PATENT DOCUMENTS

| | | |
|---|---|---|
| EP | 0 417 438 | 3/1991 |

* cited by examiner

*Primary Examiner*—John P Lacyk
(74) *Attorney, Agent, or Firm*—Thorpe North & Western LLP

(57) ABSTRACT

A device and method for sexual therapy are provided. The device can include a chamber and a negative pressure source coupled to the chamber. At least one airflow opening can be formed into the chamber and configured to allow airflow through the airflow opening. In addition, a clitoris can be located in the chamber or airflow opening. An airflow regulator is configured to be adjusted over the at least one airflow opening to enable varying amounts of airflow through the chamber and past the clitoris.

20 Claims, 5 Drawing Sheets

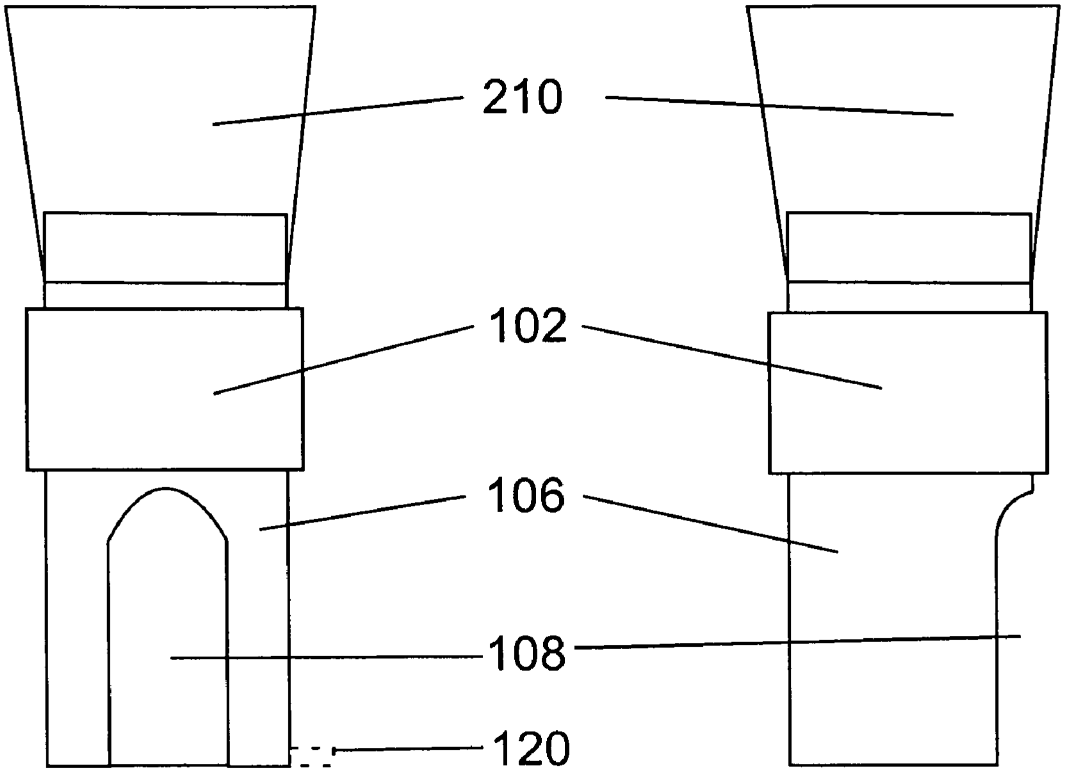
Fig. 2
Fig. 3
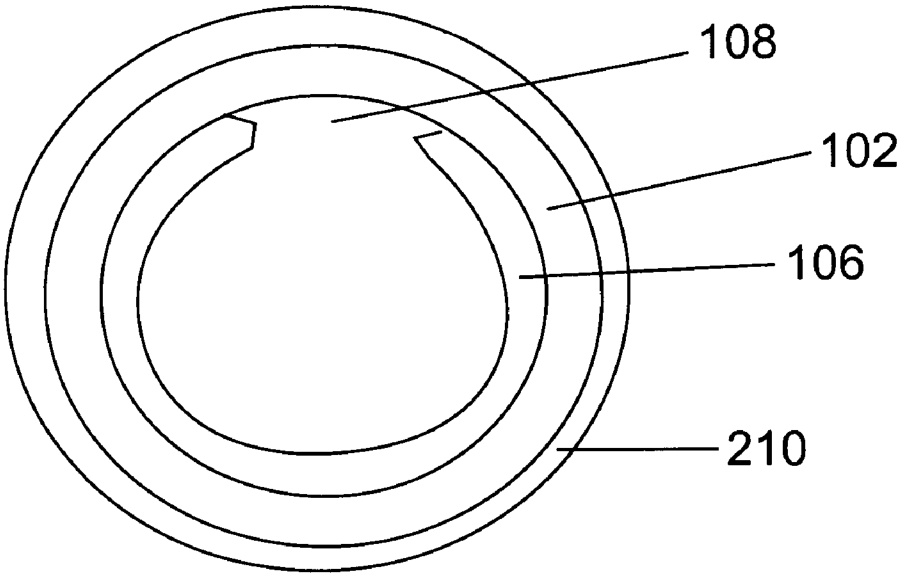
Fig. 4

SEXUAL THERAPY DEVICE

CROSS-REFERENCE TO RELATED APPLICATIONS AND PRIORITY CLAIM

This application claims priority to U.S. Provisional Patent Application Ser. No. 60/631,251 for Joanne Drysdale, entitled "Clitoris Stimulator and Orgasm Inducer Using Vacuum Suction and the Air Flow Current from the Vacuum" filed on Nov. 26, 2004.

BACKGROUND

Perhaps one of the most personal and intimate relations between people is sexual activity. If sexual activity between intimate partners becomes difficult, the entire interpersonal relationship can become strained. For some people, these sexual activity problems can rise to the level of sexual dysfunction. Sexual dysfunction includes desire, arousal, orgasm and sex pain disorders. In addition, a patients' complaints, physical symptoms, and emotions may be difficult to diagnose and treat due to the combined physical and psychological natures of such disorders.

Female Sexual Dysfunction (FSD) includes a disorder called Female Sexual Arousal Disorder (FSAD). FSAD is the persistent or recurrent inability to attain or maintain sufficient lubrication or swelling responses during sexual activity resulting in personal distress. Medical studies show that up to 43% of women may now suffer from FSD. Individuals who have FSAD can include women who are bored of sexual routines, receive inadequate stimulation (because of age or partner), or even have clitoris blood flow or engorgement problems. It is believed that ensuring clitoral tumescence (i.e., engorgement, swelling, and erection) can play an important role in solving FSAD. For some FSAD patients, it is simply enough to get past the clitoral tumescence stage and then sexual intercourse may become pleasurable again.

While some FSAD patients receive vasoactive gel to aid in blood flow for clitoral tumescence, this type of treatment is not necessarily effective for all women. As a result, non-pharmaceutical devices can be helpful in treating FSAD patients. Previous devices for clitoral stimulation have used friction, vibration and suction. Friction has the problem of potentially preventing blood flow to the clitoris and preventing tumescence. Vibration can provide stimulation to the clitoris but does not necessarily encourage tumescence, and vibration can also case irritation, soreness, and itching. Suction encourages tumescence, but does not stimulate the clitoris like vibration or friction. In fact, suction devices tend to seal the clitoris area due to the suction device structure and this may cause discomfort.

SUMMARY

A device and method for sexual therapy are provided. The device can include a chamber and a negative pressure source coupled to the chamber. At least one airflow opening can be formed into the chamber and configured to allow airflow through the airflow opening. In addition, a clitoris can be located in the chamber or airflow opening. An airflow regulator is configured to be adjusted over the at least one airflow opening to enable varying amounts of airflow through the chamber and past the clitoris.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 2 is a front view of a therapy device with one air opening in accordance with an embodiment of the present invention;

FIG. 3 is a side view of the embodiment shown in FIG. 2;

FIG. 4 is a bottom view of the embodiment shown in FIG. 2 and FIG. 3;

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

Figure 1:
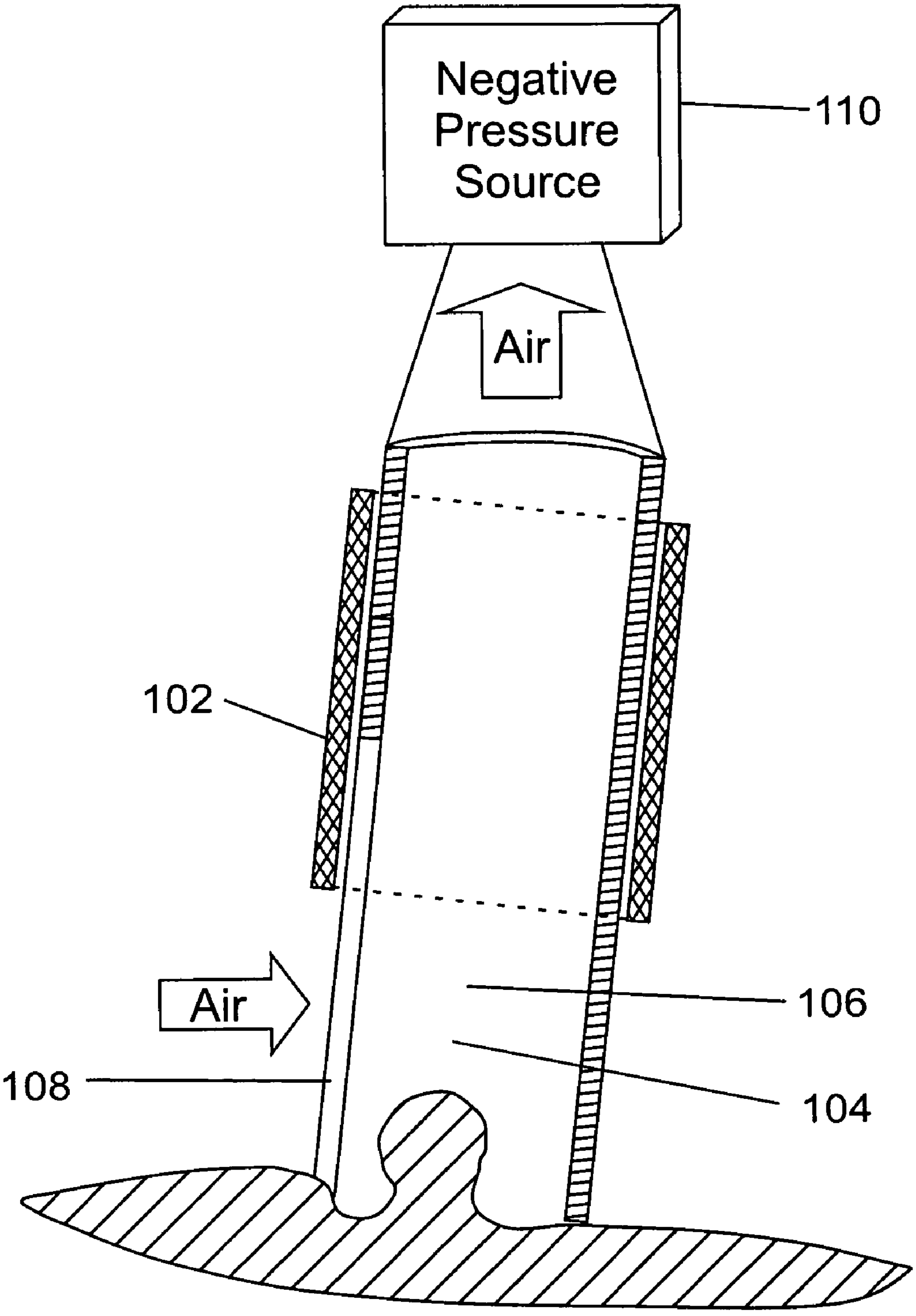
FIG. 1 is a cross-sectional view of a therapy device and clitoris in accordance with an embodiment of the present invention.

As illustrated in FIG. 1, an example embodiment of a device is provided for sexual therapy and/or stimulation using an air channel. The sexual therapy device can include a chamber 106 and a negative pressure source 110 coupled to the chamber.

At least one airflow opening 108 can be formed into the chamber 106 or airflow channel. The airflow opening of the chamber can be configured to allow airflow through the airflow opening and placement of a clitoris 104. For example, the chamber can surround the user's clitoris 104. Once the negative pressure device 110 is started, airflow passes from the airflow opening 108 at the proximal end of the chamber and past the user's clitoris 104 through the chamber 106 (or tube) and eventually into the negative pressure device 110 or vacuum. In addition, the chamber may be elongated with respect to its diameter, if desired.

An airflow regulator 102 can be configured to be adjusted one or more airflow openings to enable varying amounts of airflow through the chamber and past the clitoris. In the embodiment of FIG. 1, the airflow may be regulated by sliding the airflow regulator 102 over the airflow opening 108 of the chamber 106.

The negative pressure or vacuum helps engorge the clitoris with blood. A user may adjust the airflow regulator and clitoris position within the chamber in order to maximize the pleasurable sensation. Alternatively, the clitoris may be positioned in or near the airflow opening itself. The airflow past the clitoris can cause the clitoris to vibrate and generate desirable sensations. Once the desired effect has been achieved, the negative pressure or vacuum device may be shut off. Any type of device that provides airflow to the chamber or channel can be used with the present invention.

For some FSAD patients, this device is used so that the user's partner may continue the sexual activity once the user's clitoris has become engorged. Other patients may choose to use the device to provide stimulation in order to produce more lubrication. Once sufficient lubrication has been obtained, the user may continue sexual activity with a partner. Use of the therapy device can help break the cycle of sexual dysfunction that feeds on unsatisfied sexual experiences.

While this device and method may be beneficial to women suffering from FSD, benefits can also be realized by any members of the sexually active adult female population. By providing a device and method for fairly rapid clitoral tumescence, this allows women to be able to satisfy their needs for sexual satisfaction by being able to experience as many orgasms as she desires to reach a state of sexual satisfaction. With the clitoral movement created by the airflow, the clitoris can move like a vibrating flute reed. Some women may use the device to stimulate the genitalia to achieve additional orgasms than would otherwise be available, while other women may use the device to reach fulfillment several times due to the lack of a partner.

Since virtually any woman can reach the desired state of sexual satisfaction using the present invention, this can result in a woman having better self esteem, reduced stress, and make her more content. This increased positive mental state can have a positive result on other aspects of her life. For example, by continued clitoral tumescence, a woman may avoid the suffering related to FSD. In addition, the use of this device by all women for their satisfaction can help remove the stigma of using the device to treat FSD. This helps make women with FSD feel less inferior.

With reference to FIGS. 2 and 3, one embodiment of a female sexual therapy device includes an airflow opening 108 for the chamber or tube 106. The opening may be created with smooth edges to prevent harm to the user. The female sexual therapy device can be connected to a vacuum source (not shown) by the negative pressure device connector 210 or vacuum connector. The negative pressure device connector can be attached so that the chamber end seals well and the connector can be tapered to allow various negative pressure source tubing types to connect to the chamber. For example, the negative pressure device connector may be made of a malleable plastic material (e.g., polyethylene), rubber, or other elastic materials to enable a better seal for the negative pressure source connection.

The chamber or channel may be made from metal, composites, plastic, rubber, resin or other known materials that are useful in similar medical and consumer applications. One embodiment may use injection molded plastic, which can produce a durable and washable device. This therapy device may be produced so that the individual components may be separated for individual cleaning or replacement.

A different airflow regulator 102 or vacuum device connector 210 may be substituted for the ones discussed so far. For example, the airflow regulator may be configured as rotating fins, sliding fins, channels, or airflow direction or modification structures to provide the desired airflow through openings in the chamber. Alternatively, the inside of the chamber (channel) or airflow regulator there may include fins, grooves, obstacles, channels, or other air guidance surfaces to vary the airflow pattern in the chamber or channel. For example, a vortex action may action or some other airflow may be generated. Varying the airflow regulation configuration can provide different airflow patterns that result in changing sensations that meet the needs of different women. In another embodiment illustrated in FIG. 2, the female sexual therapy device includes one or more stops 120 that prevent the airflow regulator 102 from leaving the chamber 106 and thus the chamber (or tube) and regulator can be cleaned together. Similarly, the vacuum device connector (or negative airflow connector) may be permanently attached to the chamber.

FIG. 3 illustrates an end-view of the therapy device. In particular, the proximal end of the chamber 106 is shown. The bottom area of the airflow opening 108 can also be seen in relation to the proximal end. In this context, the term proximal or proximal end means the end of the chamber that can be placed against the user during device application. In addition, the proximal end may be flat, concave, convex or otherwise shaped to make the device more usable for a woman. The airflow regulator 102 is shown surrounding the chamber. As described previously, the airflow regulator can move up and down over the chamber surface to cover all or a portion of the airflow opening. The end profile of the negative airflow connector 210 is also illustrated in FIG. 4 in relation to the other elements of the present embodiment.

Figures 5, 6:
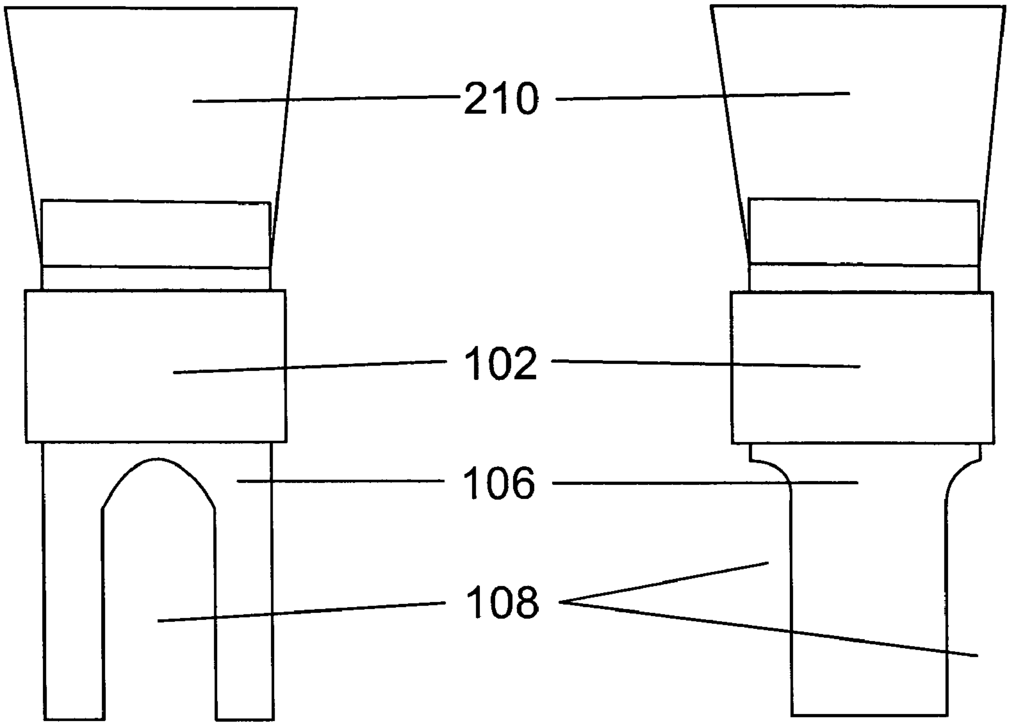
FIG. 5 is a front view of a therapy device with two air openings in accordance with an embodiment of the present invention.
FIG. 6 is a side view of the embodiment shown in FIG. 5.

In FIGS. 5 and 6, an embodiment of the invention includes a female sexual therapy device with multiple airflow openings 108. Multiple airflow openings provide different airflow patterns than a single airflow opening by directing airflow through the chamber 106 and through both the first and second airflow openings.

The airflow regulator 102 in the embodiment shown in FIGS. 5 and 6 regulates airflow for both air openings 108 simultaneously by enabling the airflow regulator to move up and down over the air openings. This configuration allows the airflow regulator to cover a portion of the airflow openings or the entire airflow openings. It is possible for other airflow regulators to regulate airflow differently between the air openings. The user may place a clitoris in either airflow opening or between both airflow openings during device use.

The airflow opening can include an opening in the sidewall and the proximal end of the therapy devices as illustrated in FIGS. 5 and 6. In addition, the airflow openings may not have an opening that extends into the proximal end of the device. For example, the airflow opening may be formed entirely in the sidewall of the chamber near the proximal end without actually creating an opening in the proximal end. This may allow the user to create a better suction fit while still allowing a desired amount of airflow to be directed toward the clitoris. Alternatively, multiple air flow openings can be located side-by-side, as opposed to being located across the chamber diameter from each other.

Figures 7, 8:
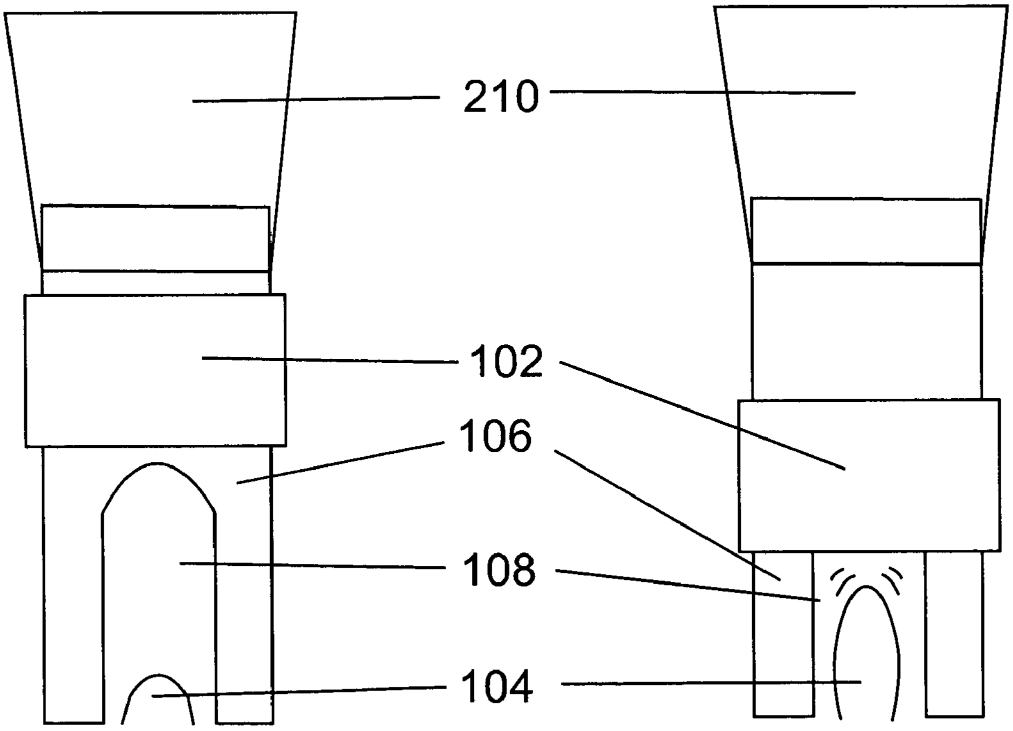
FIG. 7 is a front view of a therapy device with clitoris before air regulation and vacuum operation in accordance with an embodiment of the present invention.
FIG. 8 is a front view of a therapy device with clitoris during air regulation and vacuum operation causing stimulation and engorgement of the clitoris.

With reference to FIGS. 7 and 8, a specific embodiment of the invention is shown before and during use. FIG. 7 illustrates the female sexual therapy device before use, where a user can place her clitoris 104 near or in the airflow opening 108 contained within the chamber 106. The vacuum source (not shown here) may be connected to the vacuum device connector 210, while the airflow regulator 102 remains in an open position.

FIG. 8 then illustrates the female sexual therapy device during use, where the user's clitoris 104 has become engorged with the aid of airflow generated vibrations and suction provided by the vacuum source through the chamber or tube. The airflow regulator 102 can be moved over the airflow opening 108 causing an increased negative pressure and different airflow over the clitoris 104 through the chamber 106.

Use of the invention may be enhanced with the addition of other items. A vasoactive gel can provide another means to increase clitoral tumescence. Pharmacological agents may also aid in clitoral tumescence or sensitivity to stimulation. In addition, the device may be used with a clitoris ring or similar sensation enhancing device.

A separate vibration device can be included with or attached to the female sexual therapy device to provide further stimulation through vibration. Other oils, stimulants, and sensation enhancing compounds can also be used in combination with the present invention.

Embodiments of the invention may include safety features. An emergency valve may be added that quickly reduces airflow to the clitoris or allows the user to pulse airflow. The chamber or airflow regulator may include a grip that allows the user to firmly grasp and place the device. A hands-free connection configuration with straps or similar connection means may also be used to attach the device to the woman's body for hands-free use.

Figure 9:
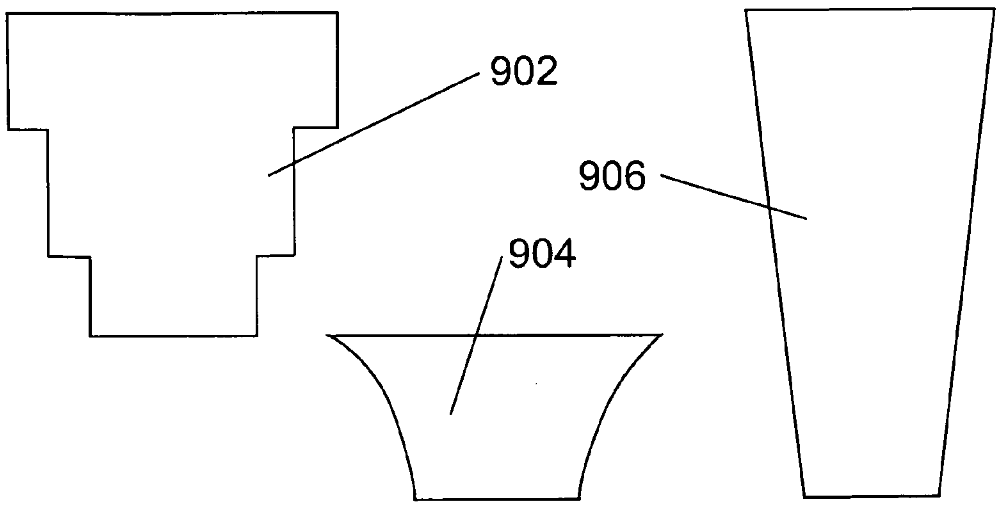
FIG. 9 is a front view of a collection of example connectors for joining a vacuum source with a therapy tube.

FIG. 9 illustrates that the embodiments may contain various negative pressure connectors including a long tapered tube 906, a horn shaped connector 904 or a stepped cylindrical tube 902 and thereby allow the user to choose a best fit with the negative pressure source. In addition, the negative pressure connectors can be coupled to a hose or flexible tubing that connects to the negative pressure device or vacuum. Using a hose or flexible tubing enables the user of the device to situate themselves a distance from the vacuum device.

Figure 10:
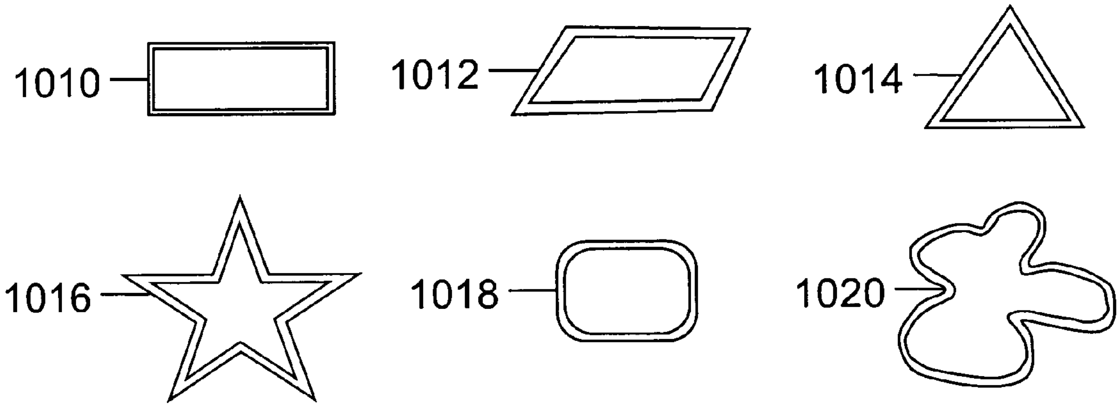
FIG. 10 illustrates proximal ends of chambers in various shape configurations in embodiments of the invention.

FIG. 10 illustrates that various chamber configurations and shapes may be used. The chamber shape may be rectangular 1010, rhombus 1012, triangular 1014, polygonal 1016, substantially oval 1018, curved 1020, may include linear and curved segments, may be irregularly shaped, or the chamber can even be spherically shaped with a pole of the sphere removed. The airflow regulator can be shaped to match the shape of the chamber and then configured to slide up and down around the outside or inside surface of the chamber.

Figure 11:
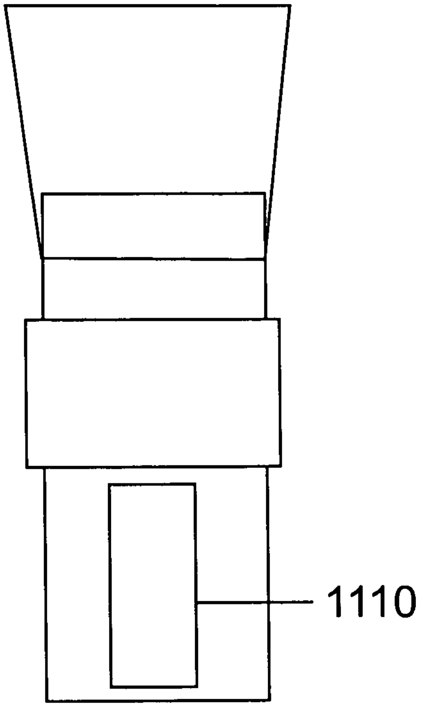
FIG. 11 illustrates an embodiment of the therapy device using a rectangular airflow opening.

FIG. 11 illustrates an embodiment using a rectangular airflow opening 1110. The shape of the opening may vary to provide varying amounts of airflow or for artistic reasons. The opening in FIG. 11 also illustrates a configuration where the opening is located completely in the chamber wall and the opening does not extend into the proximal end of the chamber. This type of configuration may allow a user to create a better seal at the proximal end while maintaining a relatively high level of airflow.

Figure 12:
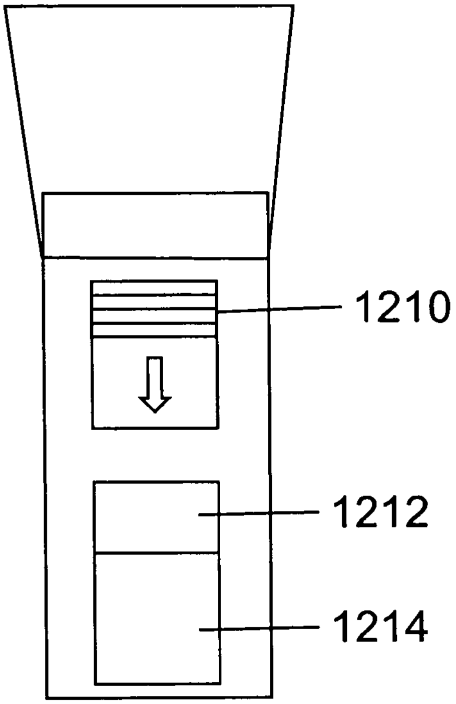
FIG. 12 illustrates an embodiment of the therapy device using an airflow regulator that is built into a chamber wall.
Figure 13:
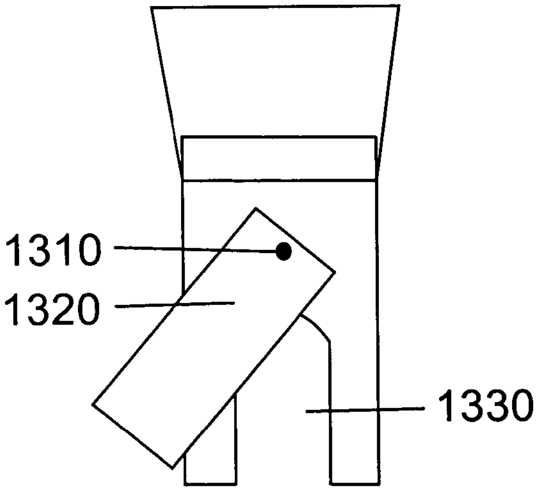
FIG. 13 illustrates an airflow regulator for the therapy device that covers the airflow opening using a pivoting cover.

FIG. 12 illustrates an embodiment of the invention using an airflow regulator that is built into a chamber wall. A thumb control location 1210 can be used on the airflow regulator 1212 to move the airflow regulator down into the opening 1214. FIG. 13 illustrates an airflow regulator that covers the airflow opening 1330 using a laterally moving door 1320 that can be moved from side to side using a pivot 1310.

In various embodiments of the invention, the negative pressure source or vacuum can be a battery-operated vacuum pump, electric pump, hand pump, and other pumps known to those in the art. Some embodiments can include an integral vacuum source attached directly to the chamber. However, such an embodiment may be somewhat noisy to an end user. In addition, the negative pressure source may be a household vacuum cleaner. Modifications for the vacuum source, use of the vacuum source, and placement of the vacuum source can be made by those skilled in the art.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A sexual therapy device, comprising:

a chamber adapted to receive a clitoris;

a negative pressure source coupled to the chamber;

an airflow opening formed at a proximal end of the chamber and configured to allow airflow through the airflow opening; and an airflow regulator movably coupled to the chamber and movable to cover at least a portion of the airflow opening to enable varying amounts of airflow through the chamber and past the clitoris.

2. A sexual therapy device as in claim 1, wherein the chamber has a proximal end and the airflow opening extends through the proximal end.

3. A sexual therapy device as in claim 1, a negative pressure source connector configured to couple the chamber to the negative pressure source.

4. A sexual therapy device as in claim 3, wherein the negative pressure source connector further comprises an elongated tube.

5. A sexual therapy device of claim 4, wherein the chamber is tapered at an end to accept the negative pressure source connector.

6. A sexual therapy device as in claim 1, wherein the negative pressure device is a vacuum.

7. A sexual therapy device as in claim 1, wherein the chamber has at least one wall configured to substantially form a cross-sectional shape selected from the group of consisting of cylindrical, square, rectangular, spherical and polygonal shapes.

8. A sexual therapy device as in claim 4, wherein the negative pressure source connector further comprises a cylindrical stepped tube.

9. A sexual therapy device as in claim 4 wherein the negative pressure source connector further comprises a tapered horn-shaped tube.

10. A sexual therapy device as in claim 1, wherein the chamber is a tube and the airflow regulator is ring shaped.

11. A sexual therapy device as in claim 10, further comprising one or more stops preventing the airflow regulator from leaving the chamber.

12. A sexual therapy device as in claim 1, wherein the chamber further comprises an emergency valve configured to enable an immediate reduction suction.

13. A sexual therapy device as in claim 1, further comprising a vibration device which enhances clitoris vibration.

14. A system to aid in stimulation therapy, comprising:

a flow channel for directing an airflow and suction for a clitoris;

a vacuum source supplying the airflow and suction to the flow channel;

an airflow regulator movably coupled to the air flow channel and movable with respect to the flow channel to modify the airflow and suction; and a vacuum device connector that joins the vacuum device and the flow channel.

15. A system as in claim 14, wherein the flow channel includes an opening in a sidewall and end of the flow channel.

16. A system as in claim 14, wherein the vacuum source is a selected from a group comprising: a household vacuum cleaner, a manual vacuum pump, and an electric vacuum pump.

17. A system as in claim 14, wherein flow channel is a tube and the airflow regulator is a ring shaped slider.

18. A method of stimulation using a stimulation device having an airflow opening, comprising:

moving an airflow regulator movably coupled to the stimulation device to interact with the airflow opening;

coupling the stimulation device to a vacuum device;

placing the stimulation device such that a clitoris is placed in proximity to the airflow opening;

starting the vacuum device to produce a vacuum effect; and adjusting the airflow regulator to provide a desired airflow through the airflow opening to maximize desired sensations.

19. The method of claim 18, further comprising placing vasoactive gel on the clitoris providing increased blood flow.

20. The method of claim 18, further comprising the step of using a clitoris ring to aid in maintaining clitoral tumescence.

* * * * *